United States Patent [19]

Dikstein et al.

[11] Patent Number: 4,610,978

[45] Date of Patent: Sep. 9, 1986

[54] COMPOSITIONS CONTAINING 1α-HYDROXYCHOLECALCIFEROL FOR TOPICAL TREATMENT OF SKIN DISORDERS AND METHODS EMPLOYING SAME

[75] Inventors: Shabtay Dikstein; Abraham Hartzshtark, both of Jerusalem, Israel

[73] Assignee: Yissum Research Development Company of the Hebrew University of Jerusalem, Jerusalem, Israel

[21] Appl. No.: 590,072

[22] Filed: Mar. 15, 1984

[30] Foreign Application Priority Data

Mar. 22, 1983 [IL] Israel .................................. 68195
Mar. 22, 1983 [IL] Israel .................................. 68196

[51] Int. Cl.$^4$ ...................... A61K 31/59; A61K 31/70
[52] U.S. Cl. ...................................... 514/46; 514/167; 514/861; 514/863
[58] Field of Search .................. 424/236; 514/167, 46

[56] References Cited

U.S. PATENT DOCUMENTS

| | | | |
|---|---|---|---|
| 3,655,881 | 4/1972 | Jackon ................................. | 424/144 |
| 3,966,777 | 6/1976 | Mazur et al. ................... | 424/236 X |
| 4,230,701 | 10/1980 | Holick et al. ....................... | 424/236 |
| 4,308,264 | 12/1981 | Conway et al. ..................... | 424/236 |
| 4,435,325 | 3/1984 | Jolly et al. ....................... | 424/236 X |

OTHER PUBLICATIONS

Chemical Abstracts 84:53879j, 1976 (Popovici).
Wells, Amer. Perf. & Essen. Oil Review, pp. 117 and 120, (1953).

Primary Examiner—Leonard Schenkman
Attorney, Agent, or Firm—John P. White

[57] ABSTRACT

Cosmetic and dermatological compositions containing 1α-hydroxycholecalciferol and a suitable carrier useful in topical treatment of skin disorders and methods employing same are disclosed. Compositions containing 1α,25-dihydroxycholecalciferol and a suitable carrier and methods employing same are also disclosed for dermatological and cosmetic uses. Various formulations of the compositions including creams, lotions, ointments and sprays are disclosed for use in accordance with this invention. The compositions and formulations may contain additional active ingredients.

26 Claims, No Drawings

COMPOSITIONS CONTAINING 1α-HYDROXYCHOLECALCIFEROL FOR TOPICAL TREATMENT OF SKIN DISORDERS AND METHODS EMPLOYING SAME

BACKGROUND OF THE INVENTION

Skin disorders as the term is used herein encompasses numerous skin conditions ranging in severity from severe dermatitis, eczema, psoriasis, etc., which have typically been treated with compositions termed "dermatological" to less severe conditions such as lack of adequate skin firmness, dermal hydration or sebum secretion, etc., which are nonetheless unsightly and may cause physical discomfort. The latter type of skin disorders typically have been treated with compositions termed "cosmetic" which are used with the aim of preserving, conditioning or protecting the skin. Dermatological and cosmetic preparations have long been sought which are effective in the topical treatment of such skin disorders and which do not produce untoward side effects, including both systemic effects and such local effects as decreased skin elasticity.

Hitherto the treatment of skin disorders has been largely based on non-specific drugs, and only limited success has been achieved. Dermatitis, for example, which may be accompanied by severe scaling, fissures, edema, oozing, erosion, itching and thickening of the skin has been commonly treated with corticosteriods. Such compounds provide symptomatic relief for some patients. Steroids, however, are known to produce many local and systemic side effects, and their long term use may not be desirable.

Similarly, Vitamin D is therapeutically effective in treating certain skin disorders, but only as dosages which are associated with undesirable side effects. Vitamin D at the dose ranges used in currently marketed topical preparations is not therapeutically effective against contact dermatitis.

Prior to this invention, no compositions were known for the topical treatment of the above-mentioned skin disorders which contain materials having both calciferol-related structure and high activity in the induction of calcium binding protein. While there has been extensive use of fish liver oil, which is rich in cholecalciferol, and of various other preparations containing ergocalciferol or cholecalciferol, such preparations are known to have only limited activity.

Ergocalciferol and cholecalciferol have also been used topically as general healing and soothing preparations, usually in concentrations no greater than five (5) micrograms/g because of concern for side effects. Such preparations, however, have achieved clinical results of only low efficacy. One possible reason for the limited efficacy of these preparations, although the inventors do not wish to be bound by this theory, is that ergocalciferol and cholecalciferol have a low potency for inducing calcium binding protein. It is known that an increase in the calcium binding protein level increases the concentration of intracellular calcium in skin cells, which in turn increases the cyclic-AMP content of the cells, see Corradino, Endocrinol., 94: 1607 (1974).

Low cyclic-AMP concentrations in skin cells are known to be associated with certain skin disorders such as psoriasis, dermatitis and alopecia. The inventors have found that low cyclic-AMP levels are also encountered in various other skin disorders such as undue skin softness and slackening of the skin. Attempts to increase the cyclic-AMP content of the skin have been described in the literature.

In pursuing this approach to the study of skin disorders, the inventors have unexpectedly discovered that particular cholecalciferol derivatives are highly effective in the treatment of certain skin disorders.

SUMMARY OF THE INVENTION

This invention relates to compositions containing 1α-hydroxycholecalciferol or 1α,25-dihydroxycholecalciferol for the topical treatment of certain skin disorders and methods of employing the disclosed compositions. In one aspect of this invention dermatological compositions for the topical treatment of disorders such as dermatitis, psoriasis, eczema, solar keratosis and certain stages of wound healing are provided. Methods employing the dermatological compositions are also provided. In another aspect of this invention, cosmetic compositions for the topical treatment of wrinkles, dry skin (lack of dermal hydration) and skin slackness (lack of skin firmness) and methods employing the cosmetic compositions are provided. The cosmetic compositions are also useful for general skin care and in combating the aging process of skin. Various formulations for the dermatological and cosmetic compositions are provided and may include additional active ingredients.

DETAILED DESCRIPTION OF THE INVENTION

The present invention provides compositions for use in the topical treatment of skin disorders which comprise an effective amount of a compound of the formula

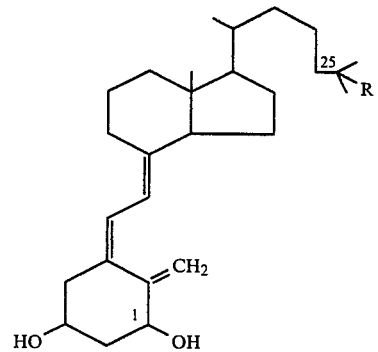

where R is H or OH, or lower alkyl esters thereof and a suitable carrier. Where R is H the compound is 1α-hydroxycholecalciferol. Where R is OH, the compound is 1α,25-dihydroxycholecalciferol.

In one aspect of this invention dermatological compositions, formulations thereof and methods of using same are provided for the topical treatment of skin disorders such as eczema; psoriasis; dermatitis; dry skin (lack of dermal hydration); solar keratosis; and certain stages of alopecia and wound healing.

Such dermatological compositions contain from about 0.03 µg to about 1.0 µg of 1α-hydroxycholecalciferol per gram of composition. Alternately, effective dermatological compositions in accordance with this invention may be prepared with 1α,25-dihydroxycholecalciferol instead of 1α-hydroxycholecalciferol. In that case, the effective amount of the dihydroxy compound is also from about 0.03 µg to about 1.0 µg per gram of the composition. Since such low dosages are required, risk of undesired side-effects and systemic effects is minimized.

The dermatological compositions are formulated preferably as creams, lotions, sprays, ointments and the like by choice of appropriate carriers. Suitable carriers include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers and antioxidants may also be included, as well as agents imparting color or fragrance if desired.

Dermatological creams are preferably formulated from a mixture of mineral oil, self-emulsifying beeswax and water in which mixture the active ingredient, preferably 1α-hydroxycholecalciferol, dissolved in a small amount of an oil such as almond oil is admixed.

Dermatological ointments may be formulated by mixing a solution of the active ingredient in an oil such as almond oil with warm white soft paraffin and allowing the mixture to cool.

Dermatological lotions may be conveniently prepared by dissolving the active ingredient, preferably 1α-hydroxycholecalciferol, in a suitable high molecular weight alcohol such as polyethylene glycol.

One or more additional substances which have therapeutic effects on the skin may also be incorporated in the dermatological compositions. Thus in one embodiment of this invention the composition also contains one or more compound capable of increasing cyclic-AMP levels in the skin. Suitable compounds include adenosine, in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include compounds capable of inducing epithelialization. Such compounds include retinoids such as Vitamin A, in an amount of about 0.003–0.3% by weight and chromanols such as Vitamin E or derivatives thereof in an amount of about 0.1–10% by weight, both based on the weight of the composition. Anti-inflammatory agents such as corticosteroids are also suitably incorporated in the compositions. Such corticosteroids include, for example, hydrocortisone or its acetate in an amount of about 0.25–5% by weight and dexamethasone, in an amount of about 0.025–0.5% by weight, both based on the weight of the composition. Also suitable for use as additional ingredients in the compositions of this invention are keratoplastic agents such as anthralin and coal tar in an amount of about 0.05–2% for anthralin and 0.1–20% for coal tar, both by weight based on the weight of the composition.

Topical application of dermatological compositions of this invention to the affected areas of the skin was found to be therapeutically effective in the treatment of dermatitis (contact and atopic) within a few days. In cases of psoriasis, topical application of dermatological compositions of this invention resulted in the disappearance of itching and scaling within a few weeks. Acceleration of wound healing was also observed. At the same time, levels of calcium and phorphorus in the blood of patients were monitored. No significant change was observed during treatment.

The therapeutic effects of compositions according to this invention were compared with the effects of compositions containing other calciferol derivatives. Patients with dermatitis (contact or atopic) were treated by the topical application of an ointment containing, in the case of a composition in accordance with this invention, 10 μg of 1α-hydroxycholecalciferol, 30 gm of almond oil and 70 gm of white soft paraffin. Patients with psoriasis were treated by the topical application of an ointment containing, in the case of a composition in accordance with this invention, 10 μg of 1α-hydroxycholecalciferol, 1000 U/g of Vitamin A dissolved in a minimum amount of vegetable oil, 30 gm of almond oil and 70 gm of white soft petrolatum. The other calciferol derivatives studied were ergocalciferol, cholecalciferol and 24,25-dihydroxycholecalciferol. An ointment containing 1α,25-dihydroxycholecalciferol was also studied and was found to be of equivalent therapeutic efficacy to ointments containing 1α-hydroxycholecalciferol. The results are summarized in Table I, which also provides the reported relative calcium binding protein inducing activity of the calciferol derivatives employed.

Table I also illustrates another advantage of the compositions of this invention in addition to efficacy in the topical treatment of dermatitis and psoriasis, i.e., that the high potency of the subject compositions may also correlate with increased safety and specificity of action over prior compositions. It is well known that ergocalciferol and cholecalciferol are absorbed into the bloodstream through the skin. Topical compositions containing ergocalciferol or cholecalciferol, especially when applied in large dosages or to large areas of the skin, may thus cause systemic effects as well as undesirable local effects. Indeed, at the high dosage of ergocalciferol indicated in Table I, systemic effects are observed with only minimal therapeutic benefit. Furthermore at active dosage levels ergocalciferol was found to decrease skin elasticity. Compositions of the present invention, however, resulted in significant therapeutic benefit at one hundredth the dosage level as prior compositions and without the systemic effects or untoward local side effects thereof.

Such high activity especially in the preferred dermatological topical compositions containing 1α-hydroxycholecalciferol is surprising in light of the generally accepted view that to become therapeutically active the compound must first be metabolized in the liver to the 1α,25-dihydroxy compound. No such topical metabolic conversion is known to take place in the skin.

TABLE I

| Clinical Efficacy of Compositions Containing Various Calciferol Derivatives | | | |
| --- | --- | --- | --- |
| Calciferol Derivative | Concentration (μg/g) | Clinical Efficacy | Relative Calcium Binding Protein Inducing Activity[a] |
| ergocalciferol | 10 | little improvement in dermatitis, no improvement in psoriasis | 1 |
| cholecalciferol | 10 | as above | 10 |
| 24,25-dihydroxy- | 10 | as above | 30 |

TABLE I-continued

Clinical Efficacy of Compositions Containing Various Calciferol Derivatives

| Calciferol Derivative | Concentration (μg/g) | Clinical Efficacy | Relative Calcium Binding Protein Inducing Activity[a] |
|---|---|---|---|
| cholecalciferol | | | |
| 1α-hydroxychole-calciferol | 0.1 | marked improvement in psoriasis, practically complete disappearance of dermatitis | 10,000 |
| 1α,25-dihydroxy-cholecalciferol | 0.1 | as above | 10,000 |

[a] As reported in Corradino, J. Steroid Brochem., Vol 9, page 1185 (1978) (assayed by organ cultured chick duodenum)

Clinical trials of a composition containing 1α-hydroxycholecalciferol also demonstrated the therapeutic efficacy of the composition in the topical treatment of contact dermatitis. The composition evaluated was an ointment containing 0.1 μg of 1α-hydroxycholecalciferol per gram of ointment in a petrolatum-almond oil base. The control composition was identical except that it did not contain the active agent 1α-hydroxycholecalciferol. The patients were treated in an out-patient clinic. They were instructed to use the preparation three times a day.

The ointment was as far as possible applied to a single lesion, or to an area of the disease, of total extent not greater than three times the volar surface of the hand. In cases of bilateral dermatitis of the hands the patient himself was able to apply the ointment to both surfaces of one hand and to the palmar surface of the other. Preferably, however, only one hand was treated with the help of an assistant, or with a disposable glove. Small amounts of the ointment were first "dotted" over the area at a distance of about 3 cm from each other, and these were merged and gently massaged into the lesion for 30 seconds. This technique was demonstrated to the patient for the first application by the investigator. The ointment and its container were weighed before the treatment started and returned with any unused contents for reweighing at the end of the treatment.

The area of the lesion treated was estimated and recorded, and the lesion photographed as required, together with suitable "control" lesions. The latter were preferably lesions of similar size and stage of development, either in the vicinity of the treated lesion or symetrically contralalateral. Relevant details of the photographic procedure were recorded so as to be reproduced when the lesions were next photographed (distance, aperture, angle, background etc.) The ointment was applied twice daily as described above, and preferably left uncovered. If a dressing was necessary, this was noted and described on the Record Sheet. The "control" lesions were left untreated, but if this were not possible the treatment used on them was noted.

Evaluations of nine (9) parameters were conducted at weekly intervals by a physician. The nine (9) parameters were redness, scaling, thickening, fissures, edema, oozing, crust formation, erosion and itching. The final evaluation was usually carried out at the end of two weeks of treatment. In isolated instances the treatment continued for up to four weeks. In this case the final score was determined at the end of the treatment period.

Table II summarizes the distribution of success or failure between patients treated with 1α-hydroxycholecalciferol and those treated with the control. The results of Table II are highly significant according to a Chi-square test.

TABLE II

COMPARATIVE EVALUATION OF THE EFFICIENCY OF TREATMENT OF CONTACT DERMATITIS WITH A COMPOSITION CONTAINING 1α-HYDROXYCHOLECALCIFEROL

| | Cases showing improvement | Cases showing no improvement |
|---|---|---|
| Ointment with 0.1 μg/gm 1α-hydroxycholecalciferol | 19 | 2 |
| Ointment without 1α-hydroxycholecalciferol | 0 | 8 |

An evaluation of the therapeutic results obtained with the twenty one (21) patients treated with the ointment containing 0.1 μg/mg 1α-hydroxycholecalciferol is summarized in Table III. Table III shows that the average overall improvement after treatment is approximately 61%. The efficacy of the treatment is poorest in alleviating redness, itching, and thickening. The lack of 100% efficacy is not due to lack of improvement of severe cases of contact dermititis. In fact some cases of contact dermatitis showed dramatic improvement, while some less severe cases showed relatively little improvement.

More complete healing may be achieved by adding 0.5% hydrocortisone acetate (w/w) to the preparation described above. This is illustrated in Table IV which summarizes the results obtained in the topical treatment of contact dermatitis with such an ointment. Surprisingly, despite the fact that the dermatitis had been treated with topical corticoids during the previous three (3) years with insufficient therapeutic effect, the addition of 0.5% (w/w) hydrocortisone acetate to the 1α-hydroxycholecalciferol composition according to this invention led to more complete healing.

Another aspect of this invention provides cosmetic compositions, formulations thereof and methods of using same for the topical treatment of such skin disorders as dry skin (lack of dermal hydration), undue skin slackness (i.e., insufficient skin firmness) and insufficient sebum secretion. The cosmetic compositions are also effective in the general preservation, conditioning and protecting of the skin, e.g., against the symptoms of aging, including wrinkles.

Cosmetic compositions for use in the above-mentioned topical treatment of skin comprise a cosmetically effective amount of 1α-hydroxycholecalciferol or 1α,25-dihydroxycholecalciferol or lower alkyl esters thereof and a suitable carrier.

TABLE III

Evaluation[a] of Therapeutic Results Obtained in the Topical Treatment of Contact Dermititis with an Ointment Containing 0.1 μg/gm 1α-hydroxycholecalciferol

| SYMPTOMS | BEFORE TREATMENT | AFTER TREATMENT | CHANGE DUE TO TREATMENT | IMPROVEMENT[b] (%) |
|---|---|---|---|---|
| Redness | 2.4 ± 0.3 | 1.3 ± 0.4 | 1.1 ± 0.3 | 45 |
| Scaling | 2.7 ± 0.2 | 1.1 ± 0.3 | 1.6 ± 0.2 | 58 |
| Thickening | 2.8 ± 0.2 | 1.4 ± 0.3 | 1.4 ± 0.2 | 50 |
| Fissures | 2.6 ± 0.3 | 0.9 ± 0.4 | 1.7 ± 0.3 | 66 |
| Edema | 2.2 ± 0.2 | 0.9 ± 0.3 | 1.3 ± 0.2 | 60 |
| Oozing | 2.1 ± 0.3 | 0.7 ± 0.7[c] | 1.4 ± 0.6 | 69 |
| Crusting | 1.9 ± 0.2 | 0.4 ± 0.3[c] | 1.6 ± 0.2 | 81 |
| Erosion | 2.1 ± 0.2 | 0.7 ± 0.4[c] | 1.4 ± 0.3 | 68 |
| Itching | 3.3 ± 0.2 | 1.8 ± 0.4 | 1.5 ± 0.3 | 51 |

[a]scoring of symptoms as follows: 0 = normal, no symptoms; 2 = moderate; 3 = marked; 4 = very marked or severe
[b]two to four weeks after start or treatment
[c]not significantly different from zero (0), $p \leq 0.05$, i.e. complete cure.

TABLE IV

Topical Treatment of Dermititis with an Ointment Containing 0.1 μg 1α-hydroxycholecalciferol per gram and 0.5% (w/w) hydrocortisone acetate

| SYMPTOMS[a] | DAY 0 | DAY 7 | DAY 14 | DAY 21 | IMPROVEMENTS (%) |
|---|---|---|---|---|---|
| Redness | 4 | 3 | 2 | 1 | 75 |
| Scaling | 4 | 4 | 1 | 1 | 75 |
| Thickening | 4 | 4 | 3 | 2 | 50 |
| Fissures | 4 | 4 | 3 | 2 | 50 |
| Pustules | 4 | 4 | 2 | 0 | 100 |
| Edema | 3 | 3 | 3 | 1 | 67 |
| Papules | 3 | 3 | 1 | 0 | 100 |
| Vesicles | 4 | 3 | 2 | 1 | 75 |
| Oozing | 4 | 1 | 0 | 0 | 100 |
| Crusts | 3 | 2 | 1 | 1 | 67 |
| Erosions | 4 | 3 | 1 | 1 | 75 |
| Itching | 4 | 4 | 3 | 0 | 100 |

[a]Scoring of symptoms as follows:
0 = normal, no symptoms;
1 = slight;
2 = moderate;
3 = marked;
4 = very marked or severe A cosmetically effective amount of either compound or a lower alkyl ester thereof for use in accordance with this invention is from about 0.001 μg to about 0.03 μg per gm of composition. A concentration of 0.01 μg per gm of the composition is preferred.

The cosmetic compositions of this invention are formulated preferably as creams, lotions, sprays, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers and antioxidants may also be included as well as agents imparting color or fragrance if desired.

Cosmetic creams are preferably formulated from a mixture of mineral oil, self-emulsifying beeswax and water in which mixture the active ingredient, preferably, 1α-hydroxycholecalciferol, dissolved in a small amount of an oil such as almond oil is admixed.

Cosmetic ointments may be formulated by mixing a solution of the active ingredient in an oil such as almond oil with warm soft paraffin and allowing the mixture to cool.

Cosmetic lotions may be conveniently prepared by dissolving the active ingredient, preferably, 1α-hydroxycholecalciferol, in a suitable high molecular weight alcohol such as polyethylene glycol.

One or more additional substances which have therapeutic effects on the skin may also be incorporated in the cosmetic compositions. Thus in one embodiment of this invention the composition also contains one or more compounds capable of increasing cyclic-AMP levels in the skin. Suitable compounds include adenosine or a nucleic acid hydrolysate in an amount of about 0.1-1% and papaverine, in an amount of about 0.5-5%, both by weight based on the weight of the composition. Also suitable are β-adrenergic agonists such as isoproterenol, in an amount of about 0.1-2% or cyclic-AMP, in an amount of about 0.1-1%, again both by weight based on the weight of the composition. Other suitable types of additional active ingredients which may be incorporated in the compositions of this invention include other compounds known to have a beneficial effect on skin. Such compounds include retinoids such as Vitamin A, in an amount of about 0.003%-0.3% by weight and chromanols such as Vitamin E or a derivative thereof in an amount of about 0.1-10% by weight, both based on the weight of the composition.

Topical application of cosmetic compositions of this invention was found to be cosmetically effective in field studies. In a typical example, topical application of an ointment containing 0.01 μg of 1α-hydroxycholecalciferol per gram of ointment to the forehead for two weeks resulted in improved skin condition. Indentometry readings decreased by 0.008 cm, reflecting improvement in dermal hydration, as measured by the method of Hartzshstark, A. and Dikstein, S., "Mechanical Testing of Human Skin in vivo", Rev. Pure Appl. Pharmacol. Sci. 3:83–122 (1983). Skin slackness decreased by 30%, as measured by levarometry, see id; the hourly rate of sebum secretion was almost doubled as measured by sebumetry, see id; and the general smoothness and appearance of the skin was markedly improved.

The cosmetic efficacy of compositions containing 1α-hydroxycholecalciferol or 1α,25-dihydroxycholecalciferol in accordance with this invention was compared with that of compositions containing other calciferol-related compounds. The results are summarized in Table V. As Table V illustrates topical application of cosmetic compositions according to the present invention increased dermal hydration and decreased skin slackness without adversely affecting skin elasticity.

Such activity is in marked contrast with that of compositions containing ergocalciferol or cholecalciferol. Topical application of compositions containing ergocalciferol, for instance, were of low cosmetic efficacy and in fact resulted in decreased skin elasticity (Table V). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Since cosmetic compositions in accordance with this invention may contain less than one hundredth of the minimum active dose of ergocalciferol or cholecalciferol, no systemic effect was expected or observed.

TABLE V

Comparative Cosmetic Effects of Compositions Containing Selected Calciferol-Related Compounds[a]

| Compound | Concentration[b] ($\mu$g/ml) | Maximum Decrease in Indentometry (cm)[c] | Elastic Recovery Decrease[d] | Decrease in Skin Slackness (Levarometry)[e] | Duration of Effects (hrs) | Relative Calcium Binding Protein Induction[f] |
|---|---|---|---|---|---|---|
| 7-dehydro-cholesterol | 15 | 0.000 | very large | none | 24 | unknown |
| ergocalciferol | 7.5 | 0.010 | significant | slight | 7 | 1 |
|  | 2.5 | no effect | none | none | 0 |  |
| cholecalciferol | 7.5 | 0.011 | none | significant | 9 | 10 |
|  | 2.7 | no effect | none | none | 0 |  |
| 24,25-dihydroxy-cholecalciferol | 7.5 | 0.004 | none | none | 0 | 30 |
| 1$\alpha$-hydroxychole-calciferol | 0.01 | 0.007 | none | significant | 7 | 10,000 |
|  | 0.03 | 0.010 | none | large | 9 |  |
| 1$\alpha$,25-dihydroxy-cholecalciferol | 0.03 | 0.010 | none | large | 9 | 10,000 |

[a]Methods of Dikstein et al., Bioengineering and the Skin (Lancaster: MTP Press, 1981), pp. 54–53
[b]Dissolved in acetone or vegetable oil or olive oil (lavarometry)
[c]In essence measures improved dermal hydration, Hartzshark, et al., Rev. Pure Appl. Pharm. Sci. 3: 83-122- (1982)
[d]in essence measures skin elasticity; decrease indicated less elastic or deteriorated skin
[e]a measurement of wrinkles or tendency to wrinkle, as due to aging
[f]values obtained by Corradino, R. A., J. Steroid Biochem., Vol. 9, page 1185 (1978)

The following examples illustrate embodiments of this invention.

EXAMPLE 1

Dermatological Cream Containing 1$\alpha$-hydroxycholecalciferol

In 1 gm of almond oil was dissolved 10 $\mu$g of 1$\alpha$-hydroxycholecalciferol. To this solution was added 40 gm of mineral oil and 20 gm of self-emulsifying beeswax. The mixture was heated to liquify. After the addition of 40 ml hot water, the mixture was mixed well. The resulting cream contains approximately 0.1 $\mu$g of 1$\alpha$-hydroxycholecalciferol per gram of cream.

EXAMPLE 2

Dermatological Cream Containing 1$\alpha$,25-dihydroxycholecalciferol

In 1 gm of almond oil was dissolved 10 $\mu$g of 1$\alpha$,25-dihydroxycholecalciferol. To this solution was added 40 gm of mineral oil and 20 gm of self-emulsifying beeswax. After the addition of 40 ml hot water, the mixture was mixed well. The resulting cream contains approximately 0.1 $\mu$g of 1$\alpha$,25-dihydroxycholecalciferol per gram of cream.

EXAMPLE 3

Dermatological Ointment Containing 1$\alpha$-hydroxycholecalciferol

In 30 gm of almond oil was dissolved 10 $\mu$g of 1$\alpha$-hydroxycholecalciferol. To this solution was added 70 gm of white soft paraffin which had been warmed just enough to be liquified. The ointment was mixed well and allowed to cool. This ointment contains approximately 0.1 $\mu$g 1$\alpha$-hydroxycholecalciferol per gram of ointment.

EXAMPLE 4

To the ointment of Example 3 was added with thorough mixing 0.5 gm of adenosine and 2.0 gm of papaverine base, both dissolved in a minimum quantity of dimethyl sulfoxide. The additional ingredients are present to the extent of about 0.5 wt % (adenosine) and 2 wt % (papaverine base).

EXAMPLE 5

To the ointment of Example 3 was added with thorough mixing 10,000 U of Vitamin A dissolved in a minimum quantity of vegetable oil. The resultant ointment contains about 100 U Vitamin A per gram of the ointment.

EXAMPLE 6

Dermatological ointments are prepared as in Example 3, 4 and 5 but with 1$\alpha$,25-dihydroxycholecalciferol substituted for 1$\alpha$-hydroxycholecalciferol.

EXAMPLE 7

Dermatological Lotion Containing 1$\alpha$-hydroxycholecalciferol

A dermatological lotion is prepared by dissolving 10 $\mu$g of 1$\alpha$-hydroxycholecalciferol in 100 gm of dry propylene glycol. The lotion is stored in a refrigerator in a brown bottle and contains about 0.1 $\mu$g of 1$\alpha$-hydroxycholecalciferol per gram of lotion.

EXAMPLE 8

Dermatological Lotion Containing 1$\alpha$,25-dihydroxycholecalciferol

A dermatological lotion is prepared according to Example 7, but with 1$\alpha$-25-dihydroxycholecalciferol substituted for 1$\alpha$-hydroxycholecalciferol.

EXAMPLE 9

Cosmetic Cream Containing 1α-hydroxycholecalciferol

In 1 gm of almond oil is dissolved 2 μg of 1α-hydroxycholecalciferol. To the solution is added 40 gm of mineral oil and 20 gm of self-emulsifying beeswax, followed by 40 ml of hot water. The mixture is mixed well to produce a cosmetic cream containing about 0.02 μg of 1α-hydroxycholecalciferol per gram of cream.

EXAMPLE 10

To a cosmetic cream prepared according to Example 9 was added 100 mg adenosine. The cream was mixed well and contains about 0.1 wt % adenosine.

EXAMPLE 11

Cosmetic creams were prepared according to Examples 9 and 10, but with 1α,25-dihydroxycholecalciferol substituted for 1α-hydroxycholecalciferol.

EXAMPLE 12

Cosmetic Ointment Containing 1α-hydroxycholecalciferol

In 30 gm of almond oil was dissolved 1 μg of 1α-hydroxycholecalciferol. To the solution so produced was added 70 gm white soft paraffin which had been warmed just enough to be liquified. The ointment was mixed well and allowed to cool. The ointment so produced contains about 0.01 μg of 1α-hydroxycholecalciferol per gram of ointment.

EXAMPLE 13

To the cosmetic ointment of Example 12 was added with thorough mixing 200 U/gm Vitamin A dissolved in a minimum amount of vegetable oil.

EXAMPLE 14

Cosmetic ointments were prepared according to Examples 12 and 13 but with 1α,25-dihydroxycholecalciferol substituted for 1α-hydroxycholecalciferol.

EXAMPLE 15

Cosmetic Lotion Containing 1α-hydroxycholecalciferol

A cosmetic lotion is prepared by dissolving 3 μg of 1α-hydroxycholecalciferol in 100 gm of dry propylene glycol. The lotion is stored in a refrigerator in a brown bottle and contains about 0.03 μg 1α-hydroxycholecalciferol per gram of lotion.

EXAMPLE 16

A cosmetic lotion is prepared according to Example 15 but with 1α,25-dihydroxycholecalciferol substituted for 1α-hydroxycholecalciferol.

What is claimed is:

1. A composition for use in topical treatment of skin disorders selected from the group consisting of dermatitis, eczema, psoriasis, lack of adequate skin firmness, dermal hydration and sebum secretion, which comprises between about 0.001 μg and 1.0 μg per gram of the composition of a compound of the formula:

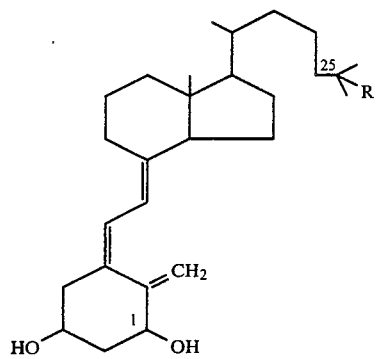

wherein R is H or OH, and a suitable carrier selected from the group consisting of a cream, an ointment and a lotion.

2. A composition according to claim 1, wherein R is H.

3. A cosmetic composition comprising a composition according to claim 1, wherein the effective amount is from about 0.001 μg/gm to about 0.03 μg/gm of the composition.

4. A dermatological composition comprising a composition according to claim 1, wherein the effective amount is from about 0.03 μg/gm to about 1 μg/gm of the composition.

5. A cream useful in the topical treatment of skin disorders comprising a composition according to claim 1, wherein the suitable carrier comprises a mixture of water, self-emulsifying beeswax, mineral oil and almond oil.

6. A cream according to claim 5, wherein the mixture includes in the following proportions:
water, about 40 parts;
self-emulsifying beeswax, about 20 parts;
mineral oil, about 40 parts; and
almond oil, about 1 part.

7. An ointment useful in the topical treatment of skin disorders comprising a composition according to claim 1, wherein the suitable carrier comprises a mixture of vegetable oil and white soft paraffin.

8. An ointment according to claim 7, wherein the vegetable oil is almond oil which is present in the amount of about 30% and the white soft paraffin is present in the amount of about 70%, both on the basis of weight.

9. A lotion useful in the topical treatment of skin disorders comprising a composition according to claim 1, wherein the suitable carrier comprises propylene glycol.

10. A composition according to claim 1 which further comprises an effective amount of a compound capable of inducing epithelialization.

11. A composition according to claim 10, wherein the compound is a retinoid.

12. A composition according to claim 11, wherein the retinoid is Vitamin A and the effective amount is about 0.003–0.3% by weight based on the weight of the composition.

13. A composition according to claim 10, wherein the compound is a chromanol.

14. A composition according to claim 13, wherein the chromanol is Vitamin E and the effective amount is about 0.1–10% by weight based on the weight of the composition.

15. A composition according to claim 1 which further comprises an effective amount of a β-agonist.

16. A composition according to claim 15, wherein the agonist is isoproterenol and the effective amount is about 0.1–2% by weight based on the weight of the composition.

17. A composition according to claim 15, wherein the agonist is cyclic-AMP and the effective amount is about 0.1–1% by weight based on the weight of the composition.

18. A composition according to claim 1 which further comprises an effective amount of an anti-inflammatory agent.

19. A composition according to claim 18, wherein the anti-inflammatory agent is a corticosteroid.

20. A composition according to claim 19, wherein the corticosteroid is hydrocortisone or its acetate and the effective amount is about 0.25–5% by weight based on the weight of the composition.

21. A composition according to claim 19, wherein the corticosteroid is dexamethasone and the effective amount is about 0.025–0.5% by weight based on the weight of the composition.

22. A composition according to claim 1 which further comprises an effective amount of a keratoplastic agent.

23. A composition according to claim 22, wherein the keratoplastic agent is coal tar and the effective amount is about 0.1–20% by weight based on the weight of the composition.

24. A composition according to claim 22, wherein the keratoplastic agent is anthralin and the effective amount is about 0.05–2% by weight based on the weight of the composition.

25. A method for treating skin disorders which comprises applying an effective amount of a dermatological composition according to claim 4 topically to the skin.

26. A method for treating skin disorders which comprises applying an effective amount of a cosmetic composition according to claim 3 topically to the skin.

* * * * *